United States Patent [19]

Nickel et al.

[11] Patent Number: 4,631,477
[45] Date of Patent: Dec. 23, 1986

[54] METHOD FOR ELIMINATING SPURIOUS SIGNALS IN A MEASURING INSTALLATION FOR IDENTIFYING THE POSITION OF A RIGID BODY IN SPACE

[75] Inventors: Bernd Nickel, Lorsch; Wolfgang Schorr, Heppenheim, both of Fed. Rep. of Germany

[73] Assignee: Siemens Aktiengesellschaft, Berlin and Munich, Fed. Rep. of Germany

[21] Appl. No.: 632,298

[22] Filed: Jul. 19, 1984

[30] Foreign Application Priority Data

Aug. 1, 1983 [DE] Fed. Rep. of Germany ....... 3327742

[51] Int. Cl.$^4$ ............................ G01B 7/14; A61B 5/10
[52] U.S. Cl. ..................................... 324/207; 128/777; 324/225; 328/165
[58] Field of Search ............... 324/207, 208, 202, 225, 324/226, 227, 228, 234, 235, 239, 251, 252, 260–262; 328/158, 165; 128/653, 774, 782, 654, 776, 777; 364/736; 434/51, 186

[56] References Cited

U.S. PATENT DOCUMENTS

| | | | |
|---|---|---|---|
| 3,439,358 | 4/1969 | Salmons | 128/653 X |
| 3,528,402 | 9/1970 | Abramowitz | 324/219 X |
| 3,537,019 | 10/1970 | Reichard | 328/165 |
| 3,648,176 | 3/1972 | Martin et al. | 328/165 X |
| 3,649,922 | 3/1972 | Ralph et al. | 328/165 X |
| 3,652,927 | 3/1972 | Uemura | 324/208 |
| 3,822,694 | 7/1974 | Mills | 128/653 X |
| 3,906,384 | 9/1975 | Schiffman | 328/165 |
| 3,927,308 | 12/1975 | Summers et al. | 328/158 X |
| 4,093,923 | 6/1978 | McCormick | 328/165 |
| 4,197,855 | 4/1980 | Lewin | 128/653 |
| 4,365,196 | 12/1982 | Finch | 324/207 |
| 4,371,836 | 2/1983 | Nickel et al. | 324/207 |
| 4,386,405 | 5/1983 | Lewin et al. | 128/777 X |

FOREIGN PATENT DOCUMENTS

| | | | |
|---|---|---|---|
| 2814551 | 10/1979 | Fed. Rep. of Germany | 324/207 |
| 1582409 | 1/1981 | United Kingdom | 324/207 |

Primary Examiner—Reinhard J. Eisenzopf
Assistant Examiner—Warren S. Edmonds
Attorney, Agent, or Firm—Hill, Van Santen, Steadman & Simpson

[57] ABSTRACT

A method for measuring the position, attitude and/or positional or attitudinal change of a fixed body in space, such as the lower jaw of a patient in a dental examination, utilizes signals obtained from a number of magnetic flux pickup blocks arranged at a distance from a magnetic field generator, the magnetic field generator being disposed on or a short distance from the fixed body and generating a defined irregular field. The pickup blocks detect the field flux, or the field flux alteration, during a measurement. In order to eliminate interference signals occurring in the region of the measuring system the signals from all of the pickup blocks are first added and the aggregate interference signals formed therefrom are respectively subtracted from the individual pickup block signals.

3 Claims, 5 Drawing Figures

METHOD FOR ELIMINATING SPURIOUS SIGNALS IN A MEASURING INSTALLATION FOR IDENTIFYING THE POSITION OF A RIGID BODY IN SPACE

BACKGROUND OF THE INVENTION

1. Field of the Invention

The present invention relates to a method for measuring the position, attitude and/or positional or attitudinal change of a fixed body in space, and in particular for measuring the position, attitude and/or positional or attitudinal change of the lower jaw of a patient undergoing a dental examination.

2. Description of the Prior Art

An apparatus as disclosed in U.S. Pat. No. 4,371,836 having a magnetic field generator which generates a defined irregular field and a plurality of pickups disposed at an interval from the field generator, the pickups having field flux-dependent sensor elements for sensing the field flux or a change in the field flux. An electronic circuit evaluates the signals from the sensor. The reference points for the pickups are disposed so as to form the corner points of a cube, and the field generator is disposed within the volume defined by the cube. In order to eliminate the influence of external interference fields, the signals of two parallel surfaces of the cube are supplied to adding amplifiers which form two surface signals therefrom which, combined in a differential amplifier, provide twice the useful signal as well as an interference signal compensated to zero.

Despite these measures, field distortions resulting, for example, from the earth's magnetic field or from ferromagnetic materials which may be introduced into or close to the antenna range, cause an incomplete compensation and thus impairment of the entire measuring procedure. In this known apparatus, this problem primarily results from the fact that the signal evaluation for eliminating the interference signal is related exclusively to the antennae themselves, however, interference from other sources within the measuring range remain substantially uncompensated.

SUMMARY OF THE INVENTION

It is an object of the present invention to provide a method for evaluating signals for measuring the position, attitude and/or positional or attitudinal change of a fixed body in space which eliminates the influence of interference fields in the region of the measuring system, that is, in the region of the volume limited by the antennae, such that those interference signals cause substantially no impairment of the measuring procedure.

The above object is inventively achieved in a method for evaluating signals which are received from a plurality of antennae which are disposed so as to form the corner points of a cube. A magnetic field generator is disposed within the volume defined by the corner points for generating a defined irregular field. The magnetic field generator may be arranged directly on the fixed body, or a distance therefrom. The antennae or flux pickups or receivers are disposed a distance from the magnetic field generator and detect the magnetic field flux or flux change during a measurement. The electronic signals from all pickups are first added and an aggregate interference signal is formed therefrom, the aggregate interference signal being respectively subtracted from the individual signals of the receivers.

DESCRIPTION OF THE PREFERRED EMBODIMENTS

Figure 1:
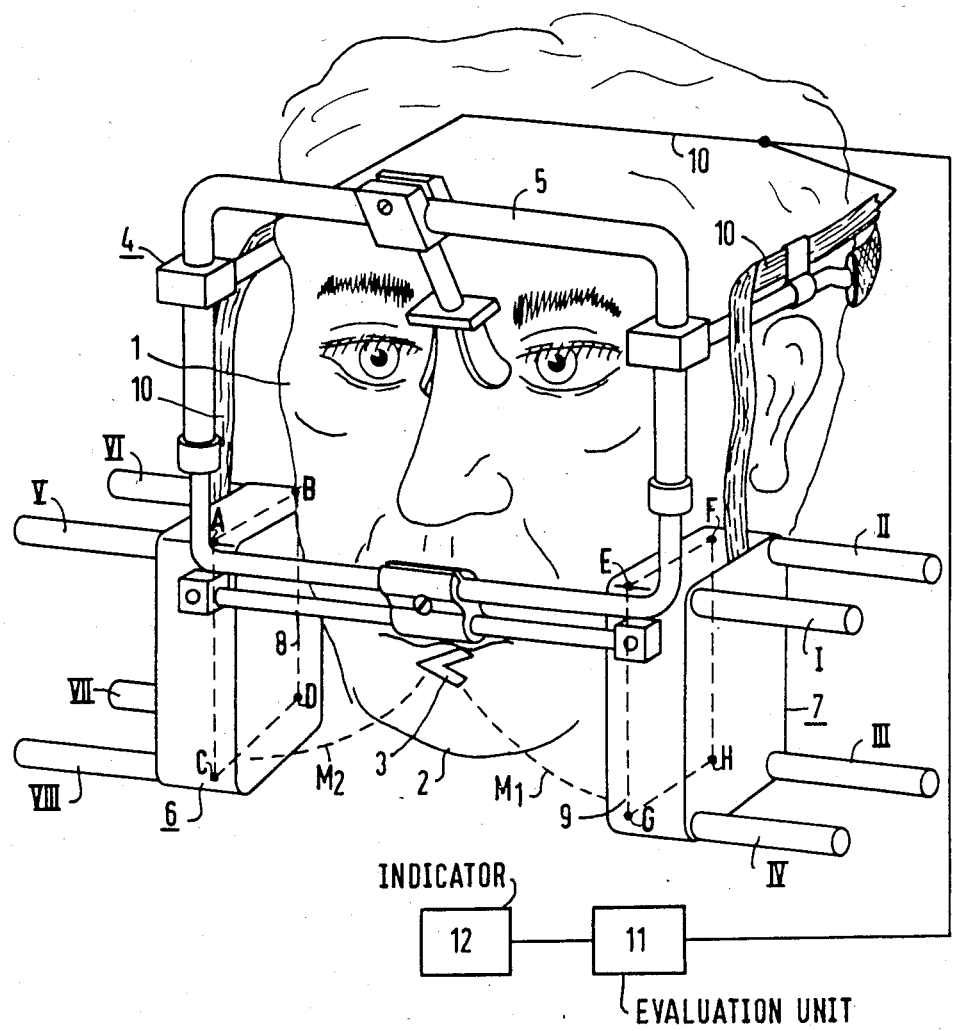
FIG. 1 is a prospective view showing an apparatus for obtaining signals for evaluation by the method disclosed and claimed herein applied to the head of a dental patient.

An apparatus for obtaining signals for evaluation in accordance with the method disclosed and claimed herein is shown in FIG. 1. Although the embodiment shown in FIG. 1 is for the purpose of evaluating such signals for identifying the position of the lower jaw of a patient undergoing a dental examination, it will be understood that the method disclosed and claimed herein can be utilized for measuring the location, attitude and/or change of location or attitude of any fixed body in space.

In FIG. 1 the apparatus is disposed for determining the position, attitude and/or positional or attitudinal change of a point of the lower jaw 2 of a patient 1. A permanent magnet 3 functioning as a magnetic field generator, is intraorally mounted at a random location on the lower jaw 2 by means of suitable adhesion or cementing means, such as by impression compound. The magnetic field generator 3 consists of two identically dimensioned bar magnets described in greater detail in U.S. Pat. No. 4,197,855. The angle defined by the two bar magnets is approximately 90°. The bar magnets are relatively small having a length of approximately 3 millimeter and a cross-section of approximately 1 square millimeter. The magnetic field generator 3 generates two irregular non-rotationally symmetric magnetic fields $M_1$ and $M_2$, indicated by the dashed lines in FIG. 1. A magnetic flux pickup unit is disposed extraorally of the patient's mouth. The unit 4 consists of a frame 5, supported on the head of the patient 1, and a pickup system having pickup blocks 6 and 7 disposed to the left and to the right of the lower jaw 2. The frame 5 is designed in a known manner as a combined glasses or head frame and contains several articulations not shown in greater detail for adaptation to various head configurations of a patient. The two pickup blocks 6 and 7 are rigidly interconnected by a rod 8 connected to the frame 5.

Each of the pickup blocks 6 and 7 contains four magnetic flux receivers; receivers I, II, III, IV being associated with pickup block 7 and receivers V, VI, VII, VIII being associated with pickup block 6. The receivers are respectively mounted in plastic housings 9 and 9a so as to be respectively disposed parallel to each other. The signals received by the magnetic flux receivers I through VIII are supplied via lines 10 to an electronic evaluation unit 11 and from there to a suitable indicator 12.

The construction and operation of the magnetic flux receivers I through VIII are described in greater detail in the aforementioned U.S. Pat. No. 4,371,836. In general, each magnetic flux receiver contains a plate-shaped Hall generator functioning as a sensor element having effective surfaces in abutment, on both sides, with antenna rods or bars comprised of mu-metal. The signals received by the magnetic flux receivers I through VIII (by means of the Hall generators) are supplied to the evaluation unit 11 amplified by a preamplifier (not shown) disposed within the housings 9 and 9a.

Figure 2:
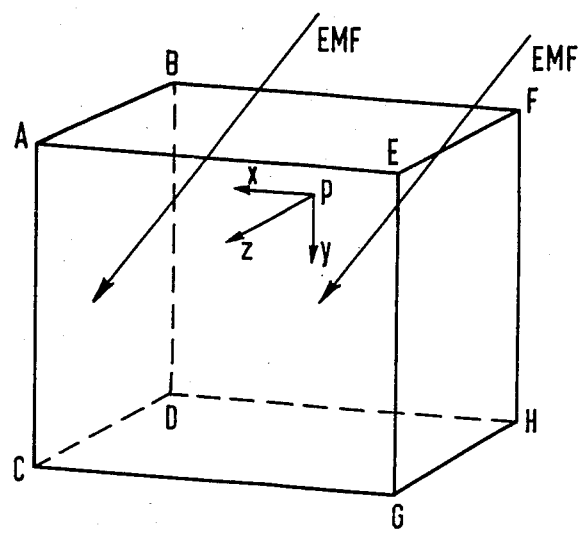
FIG. 2 is a diagram showing the cube defined by the locations of the pickups for the apparatus shown in FIG. 1.

Each of the receivers I through VIII further has a sleeve of non-ferromagnetic material into which the antenna, consisting of two parts, with the Hall generator intermediately disposed therebetween, is inserted. By the specific arrangement of the antennas and the symmetric arrangement of the Hall generators in this manner, fixed or reference points A through H are defined on the surfaces of the housings 9 and 9a, those surfaces being directly adjacent to the patient's head. The four points on each surface of the housings 9 and 9a form a square, each square forming an end face of a parallelpiped. Such a parallelpiped is shown in FIG. 2. The magnetic field generator 3 is disposed within the area defined by the squares.

As shown in FIG. 2, the magnetic field generator 3 is assumed to be located at a point p within the volume between the squares. By virtue of the symmetric arrangement of the magnetic field receivers at the corner points A through H, representative of the antenna effect, signals X, Y and Z are obtained for movement of the lower jaw 2 (and thus of the field generator 3) in the three planes x, y and z. In the case of movement in the opposite direction, signals $-X$, $-Y$ and $-Z$ are obtained.

The method disclosed herein proceeds from the fact that, between corresponding antenna pairs, the aggregate signal of both antennae is independent of the movement of the field generator 3 in the direction of a line connecting both antennae, this aggregate signal representing a measure of the size of the interference field, which is designated in FIG. 2 and subsequent figures as EMF. Thus, for example, for movement in the x-direction, the relation for the point A is: $A = x + EMF$; the relation for the point E is: $E = -x + EMF$; and the relation for A plus E is: $A + E = 2 \cdot EMF$. Analogous relations apply for the y-direction and the z-direction.

In accordance with the method disclosed herein, the electric signals of all eight antennae are added, the resulting sum of signals A to H equaling 8 EMF. This aggregate signal, as demonstrated above, is independent of the movement of the field generator 3. Because the sum of all eight antennae signals is included in the evaluation, a representative signal is obtained for the disturbance or interference variable, related to the volume limited by the antenna system A through H. This interference aggregate signal, which is independent of any changes in the useful signal (that is, a change in the position of the field generator 3 in space) represents a measure of the intensity of the interference field which is averaged over a considerably larger volume than in the known system disclosed in U.S. Pat. No. 4,371,836 wherein the intereference field signals were only representative of the field intensity at the respective position of the antennae.

Figure 3:
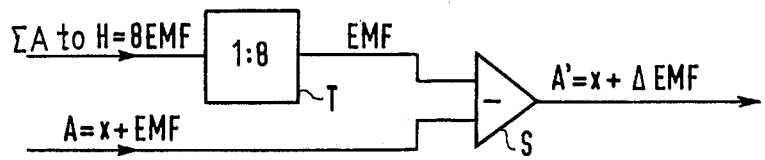
FIG. 3 is a block diagram showing a first step for signal evaluation of a reference point in accordance with the principles of the method disclosed and claimed herein.
Figure 4:
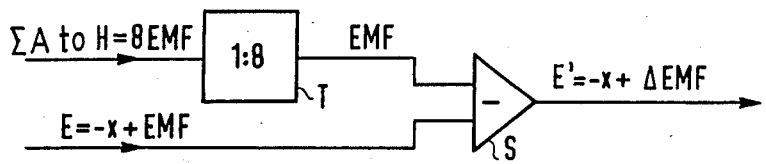
FIG. 4 is a block diagram showing the same first step for another reference point for signal evaluation in accordance with the method disclosed and claimed herein.

Compensation of interference proceeds in a compensation circuit as shown in FIGS. 3 and 4 for each reference point A through H. Compensation for point A is shown in FIG. 3 and compensation for point E is shown in FIG. 4. As shown in FIGS. 3 and 4, the sum of the intereference signals (8 EMF) is divided in a divider T by the number of antennas (8 in the present embodiment) and the resulting interference signal is subtracted from the individual signals detected at each antenna $(x + EMF, y + EMF, z + EMF \ldots)$ in a subtraction unit S. The useful signal x, y and z is obtained at the output of the subtractor s.

Remaining residual interference fields, indicated in FIGS. 3 and 4 by $\Delta EMF$, can be eliminated by subtracting the signals of two reference points from each other. For example, for the points A and E there results in the x-direction: $A' = x + \Delta EMF$ and $E' = -x + \Delta EMF$, so that $A' - E' = 2 \cdot x + \Delta EMF - \Delta EMF = 2x$. Analogous relations apply to the other reference points B through H.

Figure 5:
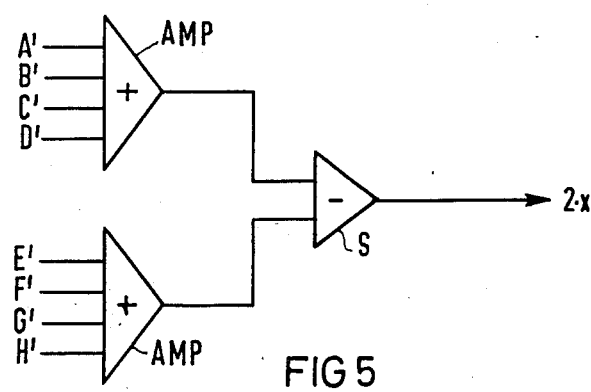
FIG. 5 is a block diagram showing a further step in the evaluation of signals in accordance with the method disclosed and claimed herein.

From the above it is apparent that a double compensation is achieved by the method disclosed herein. Compensation occurs prior to the signal processing by subtraction of the interference signals obtained from the aggregate signals of the interference fields from the individual signals, and compensation also occurs by subtraction of the individual signals already known to the present time. This latter subtraction can proceed as shown schematically in FIG. 5 wherein the signals of two parallel surfaces are first supplied to adding amplifiers AMP which form two surface signals therefrom which are subtracted in a differential amplifier S so as to provide twice the useful signal and an interference signal compensated to zero.

Although modifications and changes may be suggested by those skilled in the art it is the intention of the inventors to embody within the patent warranted hereon all changes and modifications as reasonably and properly come within the scope of his contribution to the art.

I claim as my invention:

1. A method for measuring the location of a fixed body in space by evaluating a plurality of signals respectively obtained from a plurality of magnetic flux receivers spaced from a magnetic flux generator carried on said fixed body, said receivers each having means defining the corner points of a pair of spaced parallel squared with said flux generator therebetween, each receiver generating a signal corresponding to the magnetic flux or change in magnetic flux generated by said flux generator and said signals being evaluated by the method comprising the steps of:

adding all signals from all of said receivers and thereby forming an aggregate interference signal;

subtracting said aggregate interference signal from each of the signals obtained from each receiver for eliminating the influence of external field interference from the resulting measurement.

2. A method as claimed in claim 1 comprising the additional step of dividing said aggregate interference signal by the number of magnetic flux receivers before subtracting said aggregate interference signal from each of the signals obtained from each receiver.

3. A method as claimed in claim 2 wherein said corner points defining one of said squares respectively correspond with the corner points of the other of said squares, said method comprising the additional step of subtracting signals obtained from corresponding corner points from each other after subtracting said aggregate interference signal from each of the signals obtained from each of the receivers.

* * * * *